(12) United States Patent
Sabir et al.

(10) Patent No.: US 9,597,111 B2
(45) Date of Patent: Mar. 21, 2017

(54) METHODS FOR APPLYING A SKIN GRAFT

(75) Inventors: Sameer Ahmed Sabir, Cambridge, MA (US); M Josh Tolkoff, Brookline, MA (US); Andrew Ziegler, Arlington, MA (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 12/851,682

(22) Filed: Aug. 6, 2010

(65) Prior Publication Data

US 2012/0035619 A1 Feb. 9, 2012

(51) Int. Cl.
A61B 17/322 (2006.01)
A61B 17/30 (2006.01)

(52) U.S. Cl.
CPC ...... A61B 17/322 (2013.01); A61B 2017/306 (2013.01); A61B 2017/308 (2013.01); A61B 2017/3225 (2013.01)

(58) Field of Classification Search
CPC .......... A61B 17/322; A61B 2017/3225; A61B 2017/306; A61B 2017/308
USPC ..... 606/131, 132, 167, 170; 602/53; 607/88, 607/96, 108
See application file for complete search history.

(56) References Cited

U.S. PATENT DOCUMENTS

| | | | |
|---|---|---|---|
| 2,379,574 A * | 7/1945 | Goldthwait | 8/125 |
| 3,054,404 A * | 9/1962 | Meek | 602/43 |
| 3,782,387 A * | 1/1974 | Falabella | 128/898 |
| 4,666,447 A | 5/1987 | Smith | |
| 4,773,418 A | 9/1988 | Hettich | |
| 4,917,086 A | 4/1990 | Feltovich et al. | |
| 5,015,584 A * | 5/1991 | Brysk | 424/93.7 |
| 5,386,633 A | 2/1995 | Kanno | |
| 5,441,490 A | 8/1995 | Svedman | |
| 5,460,939 A | 10/1995 | Hansbrough | |
| 5,476,478 A | 12/1995 | Jackson | |
| 5,489,304 A | 2/1996 | Orgill | |
| 5,496,339 A | 3/1996 | Koepnick | |
| 5,545,222 A | 8/1996 | Bonutti | |
| 5,571,098 A | 11/1996 | Domankevitz | |
| 5,595,570 A | 1/1997 | Smith | |
| 5,686,303 A | 11/1997 | Korman | |
| 5,730,717 A | 3/1998 | Gelbfish | |
| 5,759,193 A | 6/1998 | Burbank | |
| 5,817,115 A | 10/1998 | Nigam | |
| 5,888,219 A | 3/1999 | Bonutti | |

(Continued)

FOREIGN PATENT DOCUMENTS

| | | |
|---|---|---|
| EP | 1614404 | 1/2006 |
| WO | 9211879 | 7/1992 |

(Continued)

OTHER PUBLICATIONS

Awad, Dermatol Surg, 34(9):1186-1193, 2008.

(Continued)

Primary Examiner — Kathleen Holwerda
(74) Attorney, Agent, or Firm — Thomas Engellenner; Reza Mollaaghababa; Pepper Hamilton LLP

(57) ABSTRACT

The present invention generally relates to methods for applying a skin graft. Methods of the invention involve harvesting an epidermal skin graft, and applying the epidermal skin graft to a recipient site such that the basal layer of the skin graft makes direct contact with the recipient site.

19 Claims, 8 Drawing Sheets

(56) References Cited

U.S. PATENT DOCUMENTS

| | | |
|---|---|---|
| 5,914,264 A | 6/1999 | Korman |
| 5,921,980 A | 7/1999 | Kirn |
| 5,972,476 A | 10/1999 | Field |
| 5,976,163 A | 11/1999 | Nigam |
| 6,056,738 A | 5/2000 | Marchitto |
| 6,063,094 A | 5/2000 | Rosenberg |
| 6,071,247 A | 6/2000 | Kennedy |
| 6,080,166 A | 6/2000 | McEwen |
| 6,248,114 B1 | 6/2001 | Ysebaert |
| 6,254,580 B1 | 7/2001 | Svedman |
| 6,358,260 B1 | 3/2002 | Ross |
| 6,364,908 B1* | 4/2002 | Ysebaert ............ 623/15.12 |
| 6,402,770 B1 | 6/2002 | Jessen |
| 6,436,078 B1* | 8/2002 | Svedman .............. 604/313 |
| 6,585,939 B1 | 7/2003 | Dapprich |
| 6,623,498 B1 | 9/2003 | Ziemer |
| 6,800,282 B1 | 10/2004 | Thomson |
| 6,860,904 B2 | 3/2005 | Bonutti |
| 7,056,327 B2 | 6/2006 | Levesque et al. |
| 7,078,582 B2 | 7/2006 | Stebbings |
| 7,137,979 B2* | 11/2006 | Conrad et al. ............ 606/31 |
| 7,207,998 B2 | 4/2007 | Feingold |
| 7,208,006 B2 | 4/2007 | Fleischmann |
| 7,244,444 B2 | 7/2007 | Bates |
| 7,540,875 B2 | 6/2009 | Jessen |
| 7,625,384 B2 | 12/2009 | Eriksson |
| 7,651,507 B2 | 1/2010 | Mishra |
| 7,666,134 B2 | 2/2010 | Eriksson |
| 7,666,192 B2 | 2/2010 | Seegert |
| 7,708,746 B2 | 5/2010 | Eriksson |
| 7,926,401 B2 | 4/2011 | Mishra |
| 8,002,779 B2 | 8/2011 | Barker |
| 8,109,187 B2 | 2/2012 | Mishra |
| 8,162,957 B2 | 4/2012 | Mishra |
| 8,187,285 B2 | 5/2012 | Eriksson |
| 8,562,626 B2 | 10/2013 | Sabir |
| 2001/0029380 A1 | 10/2001 | Ysebaert |
| 2002/0052614 A1 | 5/2002 | GeBauer |
| 2003/0009185 A1 | 1/2003 | Jessen |
| 2004/0097967 A1 | 5/2004 | Ignon |
| 2004/0172045 A1 | 9/2004 | Eriksson |
| 2004/0186498 A1 | 9/2004 | Barnes et al. |
| 2004/0215217 A1 | 10/2004 | Banbury |
| 2004/0225309 A1 | 11/2004 | Eriksson |
| 2004/0230215 A1 | 11/2004 | Eriksson |
| 2004/0237744 A1 | 12/2004 | Lin |
| 2005/0038520 A1 | 2/2005 | Binette |
| 2005/0101972 A1 | 5/2005 | Bhatavadekar |
| 2005/0221276 A1 | 10/2005 | Rozakis et al. |
| 2005/0234485 A1 | 10/2005 | Seegert |
| 2006/0141616 A1 | 6/2006 | Guu |
| 2006/0258956 A1 | 11/2006 | Haberstich et al. |
| 2006/0271070 A1 | 11/2006 | Eriksson |
| 2006/0287696 A1* | 12/2006 | Wright et al. ............ 607/88 |
| 2007/0183974 A1 | 8/2007 | Pearlman |
| 2007/0255168 A1 | 11/2007 | Hibner et al. |
| 2009/0085286 A1 | 4/2009 | Grist et al. |
| 2010/0012311 A1 | 1/2010 | Colongo |
| 2010/0042127 A1 | 2/2010 | Eriksson |
| 2010/0145360 A1 | 6/2010 | Eriksson |
| 2010/0152651 A1 | 6/2010 | Boyden et al. |
| 2010/0152750 A1 | 6/2010 | Memar |
| 2010/0310823 A1 | 12/2010 | Albertelli et al. |
| 2011/0077664 A1 | 3/2011 | Schulz |
| 2011/0251602 A1 | 10/2011 | Anderson |
| 2011/0264115 A1 | 10/2011 | Asrani |
| 2012/0021186 A1 | 1/2012 | Schneider |
| 2012/0035599 A1 | 2/2012 | Sabir |
| 2012/0035618 A1 | 2/2012 | Sabir |
| 2012/0035619 A1 | 2/2012 | Sabir |
| 2012/0035620 A1 | 2/2012 | Sabir |
| 2012/0041430 A1 | 2/2012 | Anderson |
| 2012/0125798 A1 | 5/2012 | Baecker et al. |
| 2012/0172894 A1 | 7/2012 | Sabir |
| 2012/0197267 A1 | 8/2012 | Sabir |
| 2012/0201755 A1 | 8/2012 | Rozakis et al. |
| 2012/0201793 A1 | 8/2012 | Bellomo |
| 2012/0244623 A1 | 9/2012 | Patel |
| 2012/0271320 A1 | 10/2012 | Hall |
| 2013/0041385 A1 | 2/2013 | Giovannoli |

FOREIGN PATENT DOCUMENTS

| | | |
|---|---|---|
| WO | WO9528886 | 11/1995 |
| WO | 9618432 | 6/1996 |
| WO | 9633768 | 10/1996 |
| WO | 9720509 | 6/1997 |
| WO | 9816158 | 4/1998 |
| WO | 03020333 | 3/2003 |
| WO | 03039382 | 5/2003 |
| WO | 03049626 | 6/2003 |
| WO | 03049783 | 6/2003 |
| WO | 2004071313 | 8/2004 |
| WO | 2004075764 | 9/2004 |
| WO | 2004078032 | 9/2004 |
| WO | 2004105576 | 12/2004 |
| WO | 2005033273 | 4/2005 |
| WO | 2005046428 | 5/2005 |
| WO | 2007117488 | 10/2007 |
| WO | WO2010036788 | 4/2010 |
| WO | 2011038326 | 3/2011 |
| WO | 2011059441 | 5/2011 |
| WO | 2011075676 | 6/2011 |
| WO | 2012019094 | 2/2012 |
| WO | 2012019095 | 2/2012 |
| WO | 2012019096 | 2/2012 |
| WO | 2012019098 | 2/2012 |
| WO | 2012102812 | 8/2012 |
| WO | 2012145504 | 10/2012 |

OTHER PUBLICATIONS

Kreis et al., Burns, 20(1):S39-S42, 1994.
Lari et al., Burns, 27:61-66, 2001.
Mulekar et al., Dermatol Surg 25(1):66-71, 2009.
Meek, Am J Surg., 96(4):557-558, 1958.
Balaji et al., Isolation of a Novel Population of Multipotent Stem Cells From Epidermal Layer of Human Skin, Biology and Medicine, (2010), 2(2):57-67.
International Search Report and Written Opinion dated Dec. 16, 2011 for International Application No. PCT/US11/46737, 8 pages.
International Search Report and Written Opinion dated Dec. 23, 2011 for International Application No. PCT/US11/46739, 6 pages.
International Search Report and Written Opinion dated Dec. 16, 2011 for International Application No. PCT/US11/46738, 6 pages.
International Search Report and Written Opinion dated Dec. 6, 2011 for International Application No. PCT/US11/46741, 6 pages.
Office Action dated Dec. 18, 2014 for U.S. Appl. No. 13/120,799.

* cited by examiner

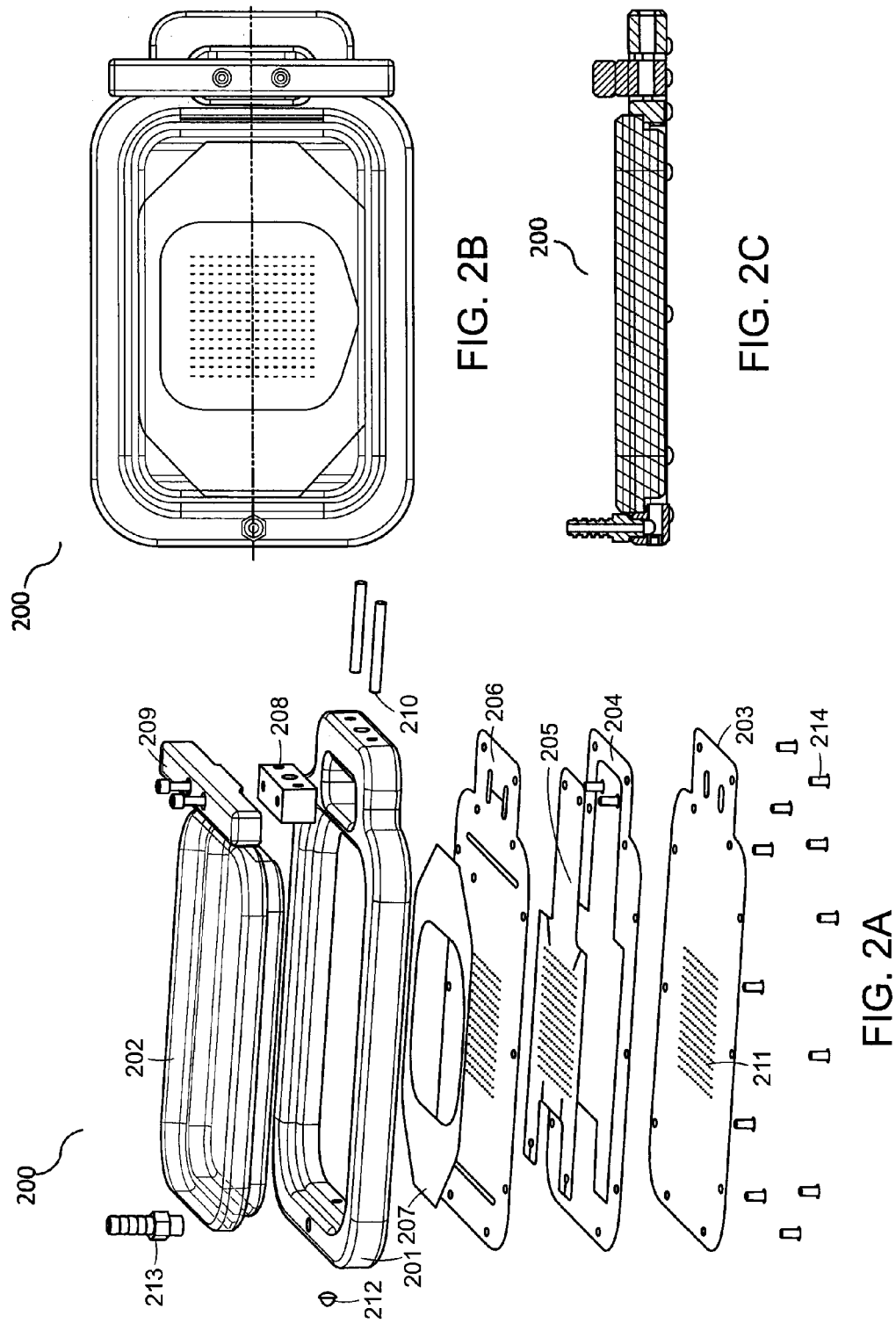

FIG. 3G
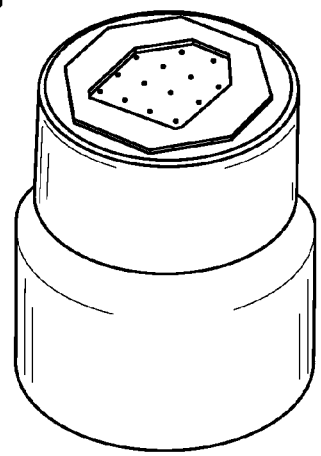
FIG. 3H
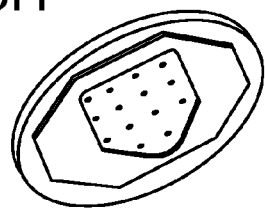
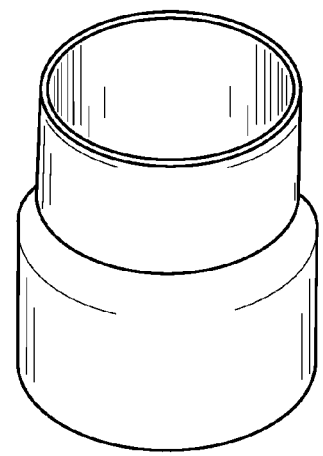
FIG. 3I
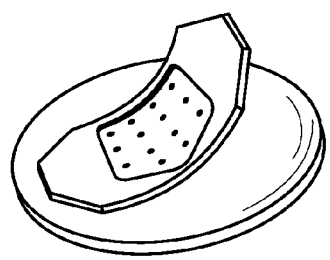

```
┌─────────────────────────────────────────────────────────┐
│  ASEPTIC SKIN CLEANING OF DONOR PIGMENTED SKIN SITE     │
└─────────────────────────────────────────────────────────┘

┌─────────────────────────────────────────────────────────┐
│               RAISE EPIDERMAL BLISTER                   │
└─────────────────────────────────────────────────────────┘

┌─────────────────────────────────────────────────────────┐
│  EPIDERMAL BLISTER IS HARVESTED FROM PIGMENTED SKIN     │
└─────────────────────────────────────────────────────────┘

┌─────────────────────────────────────────────────────────┐
│  EPIDERMAL BLISTER IS PLACED INTO A STERILE CUTTING     │
│       APPARATUS AND DIVIDED INTO MICROGRAFTS            │
└─────────────────────────────────────────────────────────┘

┌─────────────────────────────────────────────────────────┐
│      MICROGRAFTS ARE TRANSFERRED TO A STERILE           │
│              FIRST SUBSTRATE (TEGADERM)                 │
└─────────────────────────────────────────────────────────┘

┌─────────────────────────────────────────────────────────┐
│    EXPANSION OCCURS AS MICROGRAFTS RIDE ON              │
│                 FIRST SUBSTRATE                         │
│       AS SUBSTRATE SURFACE AREA IS EXPANDED             │
└─────────────────────────────────────────────────────────┘

┌─────────────────────────────────────────────────────────┐
│       EXPANDED MICROGRAFTS TRANSFERRED TO               │
│            SECOND SUBSTRATE (TEGADERM)                  │
└─────────────────────────────────────────────────────────┘

┌─────────────────────────────────────────────────────────┐
│    PATIENT VITILIGO RECIPIENT SITE IS PREPARED          │
│                  THROUGH ASEPTIC                        │
│          SKIN CLEANING AND DERMABRASION                 │
└─────────────────────────────────────────────────────────┘

┌─────────────────────────────────────────────────────────┐
│   SECOND SUBSTRATE PLUS EXPANDED MICROGRAFTS            │
│    APPLIED TO DERMABRADED PATIENT VITILIGO SITE         │
└─────────────────────────────────────────────────────────┘

┌─────────────────────────────────────────────────────────┐
│      BOTH BLISTER GENERATION (DONOR) AND                │
│              VITILIGO (RECIPIENT)                       │
│    SITE DRESSED AND WOUND CARE PROVIDED                 │
└─────────────────────────────────────────────────────────┘
```

FIG. 6

METHODS FOR APPLYING A SKIN GRAFT

FIELD OF THE INVENTION

The present invention generally relates to methods for applying a skin graft.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation (e.g., vitiligo).

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site. As with any surgical procedure, skin grafting includes certain risks. Complications may include: graft failure; rejection of the skin graft; infections at donor or recipient sites; or autograft donor sites oozing fluid and blood as they heal. Certain of these complications (e.g., graft failure and rejection of the skin graft) may be mitigated by using an autograft instead of an allograft or a xenograft.

One of the causes of graft failure is that a skin graft is applied to a recipient site having an improper orientation, i.e., the graft is applied such that the stratum corneum layer of the graft contacts the recipient site instead of the basal layer of the graft. This is a particular problem with an epidermal graft, because an epidermal graft has no blood vessels; thus, it must receive nutrients by diffusion from the underlying dermis through the basement membrane. A graft applied with an improper orientation will not receive nutrients and the cells of the graft will die, leading to graft failure.

SUMMARY

The present invention provides methods that allow for proper orientation of a skin graft on a recipient site. In particular, methods of the invention allow application of a graft to a recipient site in an orientation that allows preferred interaction between the basal layer of the graft and the donor site. In a particular embodiment, a graft or grafts are prepared and applied to a recipient site such that the proper orientation is preserved. This results in the graft being applied in an orientation that is closest to the natural orientation of the skin. Preferred grafts comprise all or substantially all epidermal layer, but grafts that have some dermal layer component also benefit from methods described herein. According to the invention an epidermal graft or an epidermal layer may comprise only or substantially only the epidermal layer (i.e., the graft may include some portion of dermal material). Methods of the invention decrease graft failure, and are particularly useful in preparing and applying epidermal grafts.

BRIEF DESCRIPTION OF THE DRAWINGS

FIG. 2 panels A-C are schematics showing a device for generating and harvesting a plurality of micrografts. Panel A provides an exploded view of the device. Panel B provides a top view of the assembled device. Panel C provides a side view of the assembled device.

FIG. 6 is a process chart showing steps for treating vitiligo using methods of the invention.

DETAILED DESCRIPTION

Figure 1:
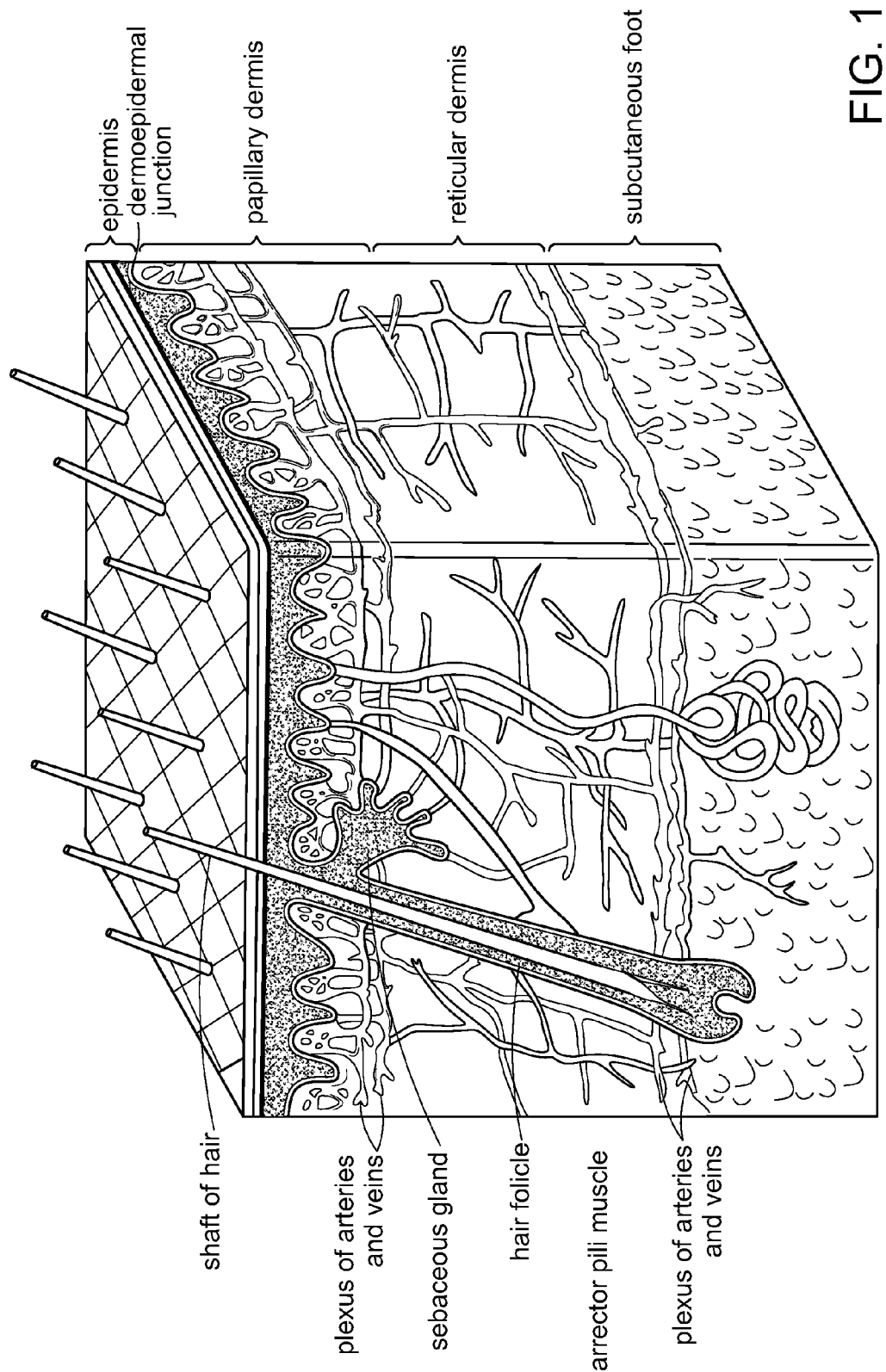
FIG. 1 is a drawing showing the anatomy of skin.
Figure 3A:
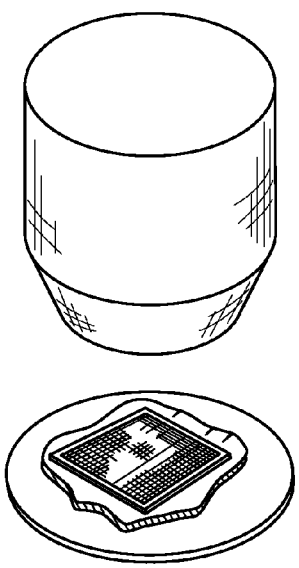
FIG. 3 provides a schematic of an exemplary process for preparing a skin graft according to methods of the invention. Panel A shows an excised epidermal blister sitting on a sterile cutting surface with a sterile cutter tool above. Panel B shows the cutter tool cutting the epidermal blister to generate an array of micrografts. Panel C shows the array of micrografts that has been produced by the cutting tool sitting on a first substrate. Panel D shows the first substrate placed into an expansion device. A second substrate is placed into the assembly cap above. Panel E shows the expansion process. As the first substrate expands, the micrografts move apart. Panel F shows that as the first substrate flattens against the assembly cap, the micrografts are transferred to the second substrate. Panel G shows the completed expansion process and that the micrografts have been transferred to the second substrate. Panel H shows removal of the assembly cap having the second substrate and expanded micrografts from the expansion device. Panel I shows removal of the second substrate having the expanded micrografts from the assembly cap of the expansion device.
Figure 3B:
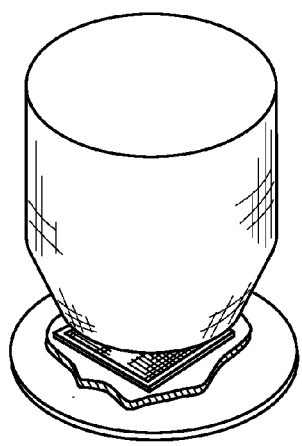
Figure 3C:
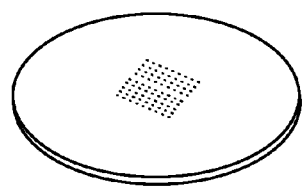
Figure 3D:
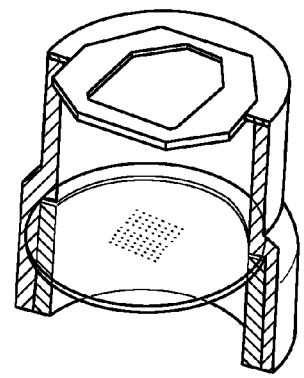
Figure 3E:
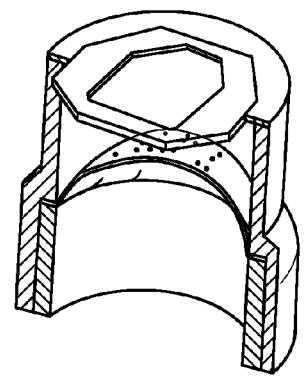
Figure 3F:
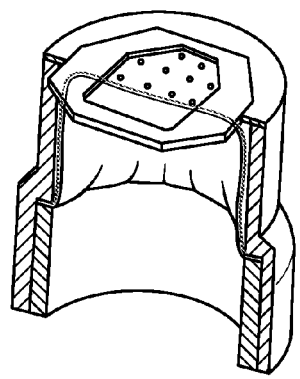

The skin consists of 2 layers. The outer layer, or epidermis, is derived from ectoderm, and the thicker inner layer, or dermis, is derived from mesoderm. The epidermis constitutes about 5% of the skin, and the remaining 95% is dermis. FIG. 1 provides a diagram showing the anatomy of skin. The skin varies in thickness depending on anatomic location, gender, and age of the individual. The epidermis, the more external of the two layers, is a stratified squamous epithelium consisting primarily of melanocytes and keratinocytes in progressive stages of differentiation from deeper to more superficial layers. The epidermis has no blood vessels; thus, it must receive nutrients by diffusion from the underlying dermis through the basement membrane, which separates the 2 layers.

The dermis is a more complex structure. It is composed of 2 layers, the more superficial papillary dermis and the deeper reticular dermis. The papillary dermis is thinner, including loose connective tissue that contains capillaries, elastic fibers, reticular fibers, and some collagen. The reticular dermis includes a thicker layer of dense connective tissue containing larger blood vessels, closely interlaced elastic fibers, and coarse, branching collagen fibers arranged in layers parallel to the surface. The reticular layer also contains fibroblasts, mast cells, nerve endings, lymphatics, and some epidermal appendages. Surrounding the components of the dermis is the gel-like ground substance composed of mucopolysaccharides (primarily hyaluronic acid), chondroitin sulfates, and glycoproteins.

Methods of the invention are directed to preparing and applying skin grafts such that the basal layer of the graft is in direct contact with the recipient site to which the graft is being applied. Maintaining the proper (i.e., natural) orientation of the graft increases the chance that the graft will survive and be accepted at the recipient site. According to the invention, graft orientation can be maintained in any manner that is desirable. For example, one can harvest a graft or grafts on a first substrate in which the basal layer of the graft(s) is oriented toward the substrate. The graft is then transferred to a second substrate, either with or without stretching on the first substrate, such that the basal layer is exposed for direct application to the recipient site. In the case in which multiple grafts or an array of grafts is used, orientation is maintained in the same manner, with the result being that the majority of grafts will be oriented properly for application to the recipient site.

In other embodiments, orientation is maintained mechanically using a single substrate for application to the recipient site. Thus, a graft is harvested as described below and placed on a substrate with the basal layer being exposed for application to a recipient site. Other methods of preserving orientation will be apparent to the skilled artisan based upon the description below.

In certain embodiments, grafts are applied directly to a recipient site in proper orientation with out the use of culturing or application of biologics or other active agents (e.g., antibiotics, growth factors, etc).

In certain embodiments, methods of the invention involve harvesting a plurality of skin grafts from a subject, applying the grafts to a first substrate, stretching the first substrate, and transferring the grafts from the first substrate to a second substrate for application to a patient recipient site.

Harvesting of the skin grafts may be accomplished by any technique known in the art, and the technique employed will depend on the type of graft required (e.g., epidermal graft, split thickness graft, or full thickness graft). An epidermal graft refers to a graft that consists of substantially epidermal skin and does not include any substantial portion of the dermal layer. A split thickness graft refers to a graft that includes sheets of superficial (epithelial) and some deep layers (dermal) of skin. A full-thickness graft refers to a graft that includes all of the layers of the skin including blood vessels.

In certain embodiments, a device as shown in FIG. 2 panels A-C is used to obtain the plurality of skin grafts. Device 200 includes a frame 201 and a lid 202. Fitted into the frame is a bottom plate 203, a cutter grid plate 204, a cutter plate 205, and a top plate 206. The bottom plate 203, the cutter plate 205, and the top plate 206, each include a hole array 211. Once assembled, the hole array 211 of each of plates 203, 205, and 206 are aligned. The size of the holes in the hole array will depend on the size of the graft needed, with larger holes being used to produce larger grafts. A first substrate 207 interacts with the top plate 206 and will receive the harvested grafts.

Device 200 further includes an actuation block 208, actuation bar 209, and actuation block guides 210. Actuation components 208, 209, and 210 control movement of the cutter plate 205. The frame 201 includes a vacuum stop 212 and the lid 202 includes a suction hole barb 213. Once assembled, the frame 201 and lid 202 are arranged such that the vacuum stop 212 and the suction hole barb 213 are aligned with each other (FIG. 1 panel B). A vacuum source is then connected to the device 200 such that negative pressure can be generated within the device. The device 200 can be held together by clamp screws 214. Device 200 may also include a heating element.

To produce and harvest the plurality of skin grafts, device 200 is placed on a donor site, such as an inner thigh of a patient. The vacuum source is turned on, producing negative pressure within device 200. The negative pressure causes the skin to be pulled toward lid 202, with a plurality of different portions of skin being pulled through each hole array 211 in each of plates 203, 205, and 206. Such action results in generation of many microblisters. The blisters may or may not be fluid-filled. Any type of raised blister may be used with methods of the invention.

Once the microblisters are raised, actuation components 208, 209, and 210 are engaged to move cutter plate 205. The movement of cutter plate 205 disrupts the alignment of the hole arrays 211 in each of plates 203, 205, and 206, and results in cutting of the microblisters. The cut microblisters are captured on the first substrate 207 that is above top plate 206. In this manner, there is provided a spaced apart array of micrografts. The amount of negative pressure applied, the amount of time the vacuum is maintained, and/or the depth of the holes above the cutting surface (plate 206) determines what type of graft will be harvested, e.g., epidermal graft, split thickness graft, or full thickness graft. Generally, each micrograft will have a lateral dimension of less than about 2 mm e.g., 100 to 2000 microns.

Once the grafts have been harvested and applied to the first substrate, the first substrate is stretched or expanded, resulting in increased distance between the individual micrografts, moving them apart and resulting in production of a skin graft that can repair a recipient site that is larger than the donor site from which the grafts were obtained. In methods of the invention, the individual grafts themselves are not expanded, i.e., the graft tissue is not stretched; rather, stretching of the substrate increases the space or distance between each individual micrograft. Methods of the invention thus minimize tissue manipulation.

The purpose of such processing is to use tissue from a donor site to cover a wound area that is larger than the donor site. The stretching of the substrate may be done manually, i.e., by hand, or may be done with the help of a machine. The stretching may be substantially uniform in all directions or may be biased in a certain direction. In a particular embodiment, the stretching is substantially uniform in all directions. Stretching of the substrate may be performed mechanically or may be accomplished by application of a pressurized fluid or gas. In certain embodiments, air pressure is used to expand the first substrate. Exemplary devices and methods are described in Korman (U.S. Pat. No. 5,914,264), the content of which is incorporated by reference herein in its entirety.

Any minimum distance can be provided between micrografts after the first substrate is stretched. The amount of stretching can be large enough to provide a sufficiently large area of substrate containing micrografts to allow a larger area of damaged tissue to be repaired using a particular amount of graft tissue removed from the donor site, i.e., the area of the stretched first substrate containing the separated micrografts can be much larger than the total area of the donor site. For example, the distance between adjacent micrografts on the stretched first substrate can be greater than about 0.5 mm, although small separation distances may also be used. For repigmentation of skin tissue, an amount of stretching can be applied to the first substrate such that the distance between adjacent micrografts is less than about 4 mm, because it is known that melanocytes, when grafted to a depigmented region, can migrate up to about 2 mm from each micrograft to repigment regions between the micrografts. This average distance can be larger if keratinocyte migration is involved with the tissue being treated because keratinocytes typically migrate greater distances compared to melanocytes.

The ratio of the wound area to the donor site area is referred to as the expansion ratio. A higher expansion ratio is desirable to minimize the trauma of the donor site, and to aid patients who have only a small amount of tissue available for grafting purposes. The amount of area expansion, e.g., the ratio of an area of damaged tissue that can be repaired compared to an area of graft tissue removed from a donor site, may be 500× or more. In particular embodiments, the area of expansion may be from about 10× to about 100×, which provides a more uniform coverage and/or repigmentation of the recipient site. For repairing burns or ulcerated tissue, the micrografts may be smaller than those used to repair other types of damaged tissue, and thus the distances between adjacent micrografts may be greater after stretching of the first substrate. In such an exemplary application, an area expansion of about 1000× or more may be used.

In other embodiments and depending on the material of the first substrate, maintaining the first substrate in a stretched configuration may result in stress on the substrate that is not optimal. Additionally, the stretched first substrate may not retain the same properties as the unstretched configuration of the first substrate, i.e., technological characteristics, such as physical, environmental and performance characteristics could be affected by the stretching of the substrate. Additionally, methods used to maintain the substrate in its stretched condition may be physically cumbersome and prevent uniform application of the micrografts to uneven skin surfaces. Thus in certain embodiments, once the first substrate has been stretched, the spaced apart micrografts are transferred to a second substrate. By transferring the micrografts to a second substrate, methods of the invention minimize manipulation and stress of the substrate that holds the graft to the recipient site.

After stretching the first substrate, the second substrate is brought into contact with the grafts on the stretched first substrate. Transfer is facilitated by the second substrate having greater affinity or more adhesive force toward the micrografts than the first substrate. In certain embodiments, the second substrate is coated with a hydrocolloid gel. In other embodiments, the first substrate is wetted with a fluid such as water or a saline solution. Wetting the micrografts and the first substrate provides lubrication between the grafts and the first substrate and allows for easy transfer of the grafts from the first substrate to the second substrate. After wetting the first substrate, the grafts have greater affinity for the second substrate than the first substrate. The wetted first substrate is then removed from the second substrate and the grafts remain attached to the second substrate. The distance between the micrografts is maintained after transfer of the micrografts from the stretched first substrate to the second substrate.

The first substrate may be made from any material that is biocompatible and capable of being stretched upon application of a moderate tensile force. The second substrate may be made from any material known in the art that is compatible with biological tissue. The second substrate may also be capable of being stretched upon application of a moderate tensile force. Exemplary materials for the first and/or second substrates include medical dressings, such as TEGADERM (medical dressing, commercially available from 3M, St. Paul, Minn.) or DUODERM (medical dressing, commercially available from 3M, St. Paul, Minn.). The first and/or second substrates may also be gas permeable.

In certain embodiments, the first and/or second substrates include an adhesive on one side that facilitates attachment of the grafts to the substrates. The substrate material may have intrinsic adhesive properties, or alternatively, a side of the substrate may be treated with an adhesive material, e.g., an adhesive spray such as LEUKOSPRAY (Beiersdoerf GmbH, Germany). In certain embodiments, the first and second substrates are the same material. In other embodiments, the first and second substrates are different materials. In certain embodiments, the materials of the first and second substrates are chosen to facilitate transfer of the micrografts from the first substrate to the second substrate. For example, in certain embodiments, the material chosen for the first substrate has a weaker adhesive than the material chosen for the second substrate.

In certain embodiments, the material of the first substrate is a deformable non-resilient material. A deformable non-resilient material refers to a material that may be manipulated, e.g., stretched or expanded, from a first configuration to a second configuration, and once in the second configuration, there is no residual stress on the substrate. Such materials may be stretched to an expanded configuration without returning to their original size, and thus in these embodiments it is not necessary to transfer the micrografts from a first substrate to a second substrate. Instead, the expanded first substrate including the micrografts is applied to a recipient site.

Such deformable non-resilient materials tend to be soft, stiff or both soft and stiff. Softness is measured on the durometer scale. An example of such a material is a soft polyurethane. A soft polyurethane is produced is as follows. Polyurethanes in general usually have soft and hard segments. The hard segments are due to the presence of phenyl bridges. In a soft polyurethane, the phenyl bridge is switched out for an aliphatic, which is more flexible as its 6 carbon ring has no double bonds. Therefore, all the segments are soft. On the Durometer Scale, a soft polyethylene is rated about Shore 80A. Other materials suitable for use with methods of the invention include low density polyethylene, linear low density polyethylene, polyester copolymers, polyamide copolymers, and certain silicones. In these embodiments, the expanded first substrate having the micrografts retains its expanded position without any residual stress, and the expanded first substrate is applied to a recipient site.

Ultimately, the grafts and substrate are applied to a recipient of site of a patient. Prior to applying the grafts to the recipient site, the site is prepared to receive the grafts using any technique known in the art. Necrotic, fibrotic or avascular tissue should be removed. The technique used to prepare the site will depend on damage to the recipient site. For example, epidermal tissue, if present at the recipient site, can be removed to prepare the area for receiving the micrografts. Burned or ulcerated sites may not need removal of epidermal tissue, although some cleaning of the site or other preparation of the site may be performed. Wounds should be debrided and then allowed to granulate for several days prior to applying the graft. Most of the granulation tissue should be removed since it has a tendency to harbor bacteria. Applying silver sulfadiazine to the wound for 10 days prior to grafting reduces the bacterial count greatly.

The size of the area at the recipient site can be about the same size as the area of the stretched first substrate having micrografts adhered thereto. This size generally will be greater than the area of the original graft tissue that was removed from the donor site to form the micrografts. The depigmented or damaged skin can be dermabraded with sandpaper or another rough material. Alternatively, the epidermal tissue can be removed from the recipient site by forming one or more blisters over the area to be treated, e.g., a suction blister or a freezing blister, and the raised epidermal blister tissue can then be removed by cutting or another procedure.

The substrate having the micrografts can be placed over the area to be treated to form a dressing. A portion of the substrate having the micrografts can be positioned over the area to be repaired, e.g., the area from which the epidermal tissue has been abraded or removed for repigmentation. The substrate can be fixed in place over the treatment area, e.g., using tape or the like. The substrate can be removed after sufficient time has elapsed to allow attachment and growth of the micrografts in the treatment area, e.g., several days to a few weeks.

Another aspect of the invention provides harvesting a single graft from a donor site, such as an epidermal graft, generating an array of micrografts from the single graft, placing the graft on a first substrate, expanding a distance between the micrografts on a first substrate, transferring the micrografts from the first substrate to a second substrate, and applying the micrografts to a recipient site. FIG. 3 provides a schematic of an exemplary process for preparing a skin graft according to methods of the invention.

Methods of the invention involve harvesting a single graft from a donor site, such as an epidermal graft. Harvesting of the skin grafts may be accomplished by any technique known in the art, and the technique employed will depend on the type of graft required (e.g., epidermal graft, split thickness graft, or full thickness graft). In certain embodiments, harvesting a skin graft involves raising a blister and cutting the blister. In certain embodiments, the blister may be a fluid-filled blister (e.g. a suction blister). In other embodiments, the blister is not fluid-filled. Any type of raised blister may be used with methods of the invention.

In certain embodiments, suction blister grafting is used. Suction blister grafting involves raising a blister, and then cutting off the raised blister. An exemplary suction blister grafting technique is shown in Awad, (Dermatol Surg, 34(9):1186-1193, 2008), the content of which is incorporated by reference herein in its entirety. This article also shows various devices used to form suction blisters. A suction blister device is also described in Kennedy et al. (U.S. Pat. No. 6,071,247), the content of which is incorporated by reference herein in its entirety. An exemplary device is commercially available from Electronic Diversities (Finksburg, Md.).

A device for raising a suction blister typically operates by use of suction chambers that are attached to a patient's skin. An instrument typically contains a power source, a vacuum pump, temperature controls and all related controls to operate multiple suction chambers. The suction chambers are connected to the console by a flexible connection. Each of the chambers is controlled by a preset temperature control to provide an optimal skin warming temperature. Both chambers share an adjustable common vacuum source that affects all chambers equally.

Blister formation is accomplished by attaching the suction blister device to a patient's skin. Typically hook & loop fastener straps are used to keep the device in place. The chamber heating system provides a slight warming of an orifice plate of the device, which is in direct contact with the patient's skin surface. The application of a moderate negative pressure from the instrument console, to the chamber interior, causes the patients skin to be gently drawn through the opening(s) in the orifice plate. The results are typical suction blisters, approximately the size of the opening(s) in the orifice plate. The skin and blister area is generally not damaged and patient discomfort is minimal.

The negative pressure chamber is fabricated of mostly plastic components, with two removable threaded caps. The upper cap is fitted with a clear viewing lens so that the actual blister formation can be observed. The opposite end of the chamber is fitted with a removable orifice plate that is placed on the patient's skin. Since this plate is simply threaded onto the chamber end, multiple plates with different opening patterns can be interchanged as desired.

The interior of the device is warmed and illuminated by an array of low voltage incandescent lamps. This lamp array is controlled from the instrument console temperature controller, cycling as needed, to maintain the set point temperature. The heat from these lamps is radiated and conducted to the orifice plate, which then warms the patient's skin. The chamber is connected to the console via a composite vacuum and low voltage electrical system. Quick connections are used for the vacuum and electrical system to facilitate removal and storage.

The Negative Pressure Instrument console is a self-contained fan cooled unit which is designed to operate on 120 VAC 60 Hz power. Vacuum is supplied by an industrial quality diaphragm type vacuum pump, capable of a typical vacuum of 20 in Hg (0-65 kpa) at 0 CFM. An analog controller that is preset to 40° C. provides the temperature control for each suction chamber. This provides accurate control of the orifice plate temperature. The instrument console has internal adjustments that allow the user to recalibrate the temperature setting if desired. Other temperatures can be preset if desired. The front panel includes a vacuum gauge and vacuum bleeder adjustment to regulate the vacuum to both chambers. The console front panel also contains the connections for the chamber assemblies.

Once the suction blister is raised, it is cut by methods known in the art (see e.g., Awad, Dermatol Surg, 34(9):1186-1193, 2008), and placed on the first substrate. Once on the first substrate, an array of micrografts are generated from the single graft. FIG. 3 panel A shows an excised skin graft on a first substrate, with a sterile cutting tool above the graft. In certain embodiments, rather than being applied directly to the first substrate, the cut blister is placed onto a sterile surface, such as a glass slide, and the array of micrografts is generated on the sterile surface prior to transfer to the first substrate. In other embodiments, the cut blister is trapped between two aligned metal screens. The screens are pushed together to cut the blister into an array of micrografts. The micrografts are then pushed out of the screens and deposited onto the first substrate using an array of pushers whose size and spacing correspond to the metal screens. In certain embodiments, the cut blister is harvested directly between the two screens for generation of the array of micrografts.

In other embodiments, the cut blister is harvested directly into a shear or punch and die device for generation of micrografts. A shear or punch die includes an array of flat-faced piston-like components that fit closely into the openings in a metal screen/mesh. In this embodiment, the cut graft is harvested onto the array of pistons, and sits between the array of pistons and the screen/mesh. The screen/mesh is closed over the cut blister and force is applied to the array of pistons. The pistons push through the holes in the screen/mesh and in the process, portions of tissue are punched out from the openings of the screen/mesh and deposited on a substrate, producing an array of micrografts on a substrate. Such embodiments allow for simultaneous generation of the array of micrografts and deposition of the array of micrografts onto the substrate.

The array of micrografts can be generated by making cuts or using other protocols to form the array of micrografts from the single graft. The cuts may pass partially or completely through the graft tissue. For example, for repigmenting skin tissue, the micrografts used may have a presence of melanocytes. Accordingly, a lateral dimension of such micrografts can be between less than about 1 mm, e.g., 200 to 1000 microns. Other exemplary sizes are between 400 and 800 microns. The area of the micrografts can be between about 0.04 mm$^2$ and about 1 mm$^2$. The exemplary sizes can provide micrografts large enough such that each micrograft is likely to contain some melanocytes, yet small enough to provide a large number of micrografts from a particular piece of graft tissue, which can facilitate a significant degree of expansion on the graft site.

For treating burns or ulcers, where presence and proliferation of keratinocytes is important, the micrograft sizes may be smaller. For example, a lateral dimension of micrografts containing keratinocytes can be between about 50 microns and about 1000 microns, or between 100 microns and about 800 microns. The area of such micrografts can be between about 0.0025 mm$^2$ and about 1 mm$^2$. The exemplary size ranges provide micrografts large enough to contain viable and undamaged keratinocytes, and small enough to facilitate repair of a larger area of damaged skin.

FIG. 3 panel B shows an exemplary cutting tool. The cutting tool may be configured in any manner, and such configuration will depend upon the size of the micrografts to be produced and the desired array pattern. The cutting tool includes a plurality of adjacent blades. The arrangement of the blades will depend upon the desired pattern for the array of micrografts. The tool shown in FIG. 3 panel B is configured to produce a square grid of micrografts (See FIG. 3 panel C). The spacing of the blades in the cutting tool will depend on the desired size of the micrografts. For example, the blades may be spaced about 100 to 2000 microns apart, or about 500 to 1000 microns apart. The cutting tool is pressed at least once into the skin graft on the first substrate to produce the array of micrografts (See FIG. 3 panels B and C).

Other exemplary devices for producing an array of micrografts include mesh devices. Such mesh devices include rigid, biocompatible material, such as stainless steel. The mesh includes a plurality of openings. The openings are sized to provide an array of micrografts of a desired size, such as lateral sizes between about 100 microns and about 1000 microns or about 300 microns to about 500 microns. Similar to the cutting tool described above, the mesh is pressed at least once into the skin graft to produce the array of micrografts.

FIG. 3 panels D-I show remaining steps of the method. Once the array of micrografts are on the first substrate, the distance between the micrografts is expanded. Expansion results in increased distance between the individual micrografts, moving them apart and resulting in production of a skin graft that can repair a recipient site that is larger than the donor site from which the grafts were obtained. Expansion may be performed as described above. After expansion of the first substrate, the second substrate is brought into contact with the grafts on the stretched first substrate for transfer of the micrografts from the expanded first substrate to the second substrate. Transfer may be performed as described above. The distance between the micrografts is maintained after transfer of the micrografts from the stretched first substrate to the second substrate. Once the grafts have been transferred to the second substrate, the grafts and substrate are applied to a recipient of site of a patient. Preparation of the recipient site and application of the array of micrografts to the prepared recipient site may be performed as described above.

In other embodiments, transfer to a second substrate is not necessary because the material of the first substrate is a deformable non-resilient material. A deformable non-resilient material refers to a material that may be manipulated, e.g., stretched or expanded, from a first configuration to a second configuration, and once in the second configuration, there is no residual stress on the substrate. Such materials may be stretched to an expanded configuration without returning to their original size. Exemplary materials are described above. In these embodiments, the expanded first substrate having the micrografts retains its expanded position without any residual stress, and the expanded first substrate is applied to a recipient site.

Preparation of the recipient site and application of the array of micrografts to the prepared recipient site may be performed as described above.

In certain aspects, methods of the invention maintain a proper orientation of a skin graft. Epidermal skin includes a stratum corneum layer and a basal layer. The stratum corneum refers to the outermost layer of the epidermis, composed of large, flat, polyhedral, plate-like envelopes filled with keratin, which is made up of dead cells that have migrated up from the stratum granulosum. This layer is composed mainly of dead cells that lack nuclei. The thickness of the stratum corneum varies according to the amount of protection and/or grip required by a region of the body. In general, the stratum corneum contains 15 to 20 layers of dead cells, and has a thickness between 10 and 40 μm.

The basal layer (or stratum germinativum or stratum basale) refers to the deepest layer of the 5 layers of the epidermis. The basal layer is a continuous layer of live cells and can be considered the stem cells of the epidermis. These cells are undifferentiated and proliferative, i.e., they create daughter cells that migrate superficially, differentiating during migration. Keratinocytes and melanocytes are found in the basal layer.

For a graft to become integrated at a recipient site, the graft must be able to receive nutrients. Since the cells of the basal layer are live cells, orienting an epidermal graft such that the basal layer interacts with the recipient site allows the graft to receive nutrients, and thus remain viable. In contrast, since the cells of the stratum corneum are dead cells, orienting an epidermal graft such that the stratum corneum layer interacts with the recipient site prevents the graft from receiving nutrients, resulting in death of the graft tissue and graft failure. Methods of the invention ensure that during the grafting process, the basal layer of a graft interacts with the recipient site of a patient, allowing for the graft to receive nutrients and thus remain viable.

Certain methods involve harvesting an epidermal skin graft, and applying the epidermal skin graft to a recipient site such that the basal layer of the skin graft makes direct contact with the recipient site. Harvesting may be accomplished by creating a blister, such as a suction blister. Suction blister grafting is described above.

In one embodiment, a vacuum is used to hold the stratum corneum side of the blister, which can be released when the blister is deposited onto the cutting surface. In other embodiments, after the blister has been raised and prior to cutting the blister, an adhesive side of a substrate is placed in contact with the stratum corneum layer of the raised blister. Upon cutting the blister, the stratum corneum layer of the graft becomes adhered to the substrate, and the basal layer is orientated away from the substrate. Such a technique ensures that the basal layer of the graft is oriented away from the substrate and is thus available to interact with the recipient site of a patient.

Other methods of the invention involve harvesting a skin graft from a donor site, placing the skin graft on a first substrate such that basal cells of the graft make direct contact with the first substrate, transferring the graft from the first substrate to a second substrate such that the basal cells do not directly contact the second substrate, and applying the second substrate to a recipient site. Harvesting may be accomplished by creating a blister, such as a suction blister. Suction blister grafting is described above. The blister is cut and the basal layer of the graft is contacted to an adhesive side of a first substrate. The basal layer of the graft becomes adhered to the first substrate and the stratum corneum layer is orientated away from the first substrate, and is available for interaction with a second substrate.

An adhesive side of a second substrate is brought into contact with the stratum corneum layer of the graft that is adhered to the first substrate. Transfer to the second substrate is accomplished as described above. Briefly, in one embodiment, the first substrate is wetted with a fluid such as water or a saline solution. Wetting the graft and the first substrate provides lubrication between the graft and the first substrate and allows for easy transfer of the graft from the first substrate to the second substrate. After wetting the first substrate, the graft has a greater affinity for the second substrate than the first substrate. The wetted first substrate is then removed from the second substrate and the grafts remain adhered to the second substrate.

Upon transfer, the stratum corneum layer of the graft becomes adhered to the second substrate, and the basal layer is orientated away from the second substrate. Such a technique ensures that the basal layer of the graft is oriented away from the second substrate and is thus available to interact with the recipient site of a patient.

Another aspect of the invention provides a devices for obtaining a skin graft. Devices of the invention include a hollow body having a distal end configured for placement on skin, a mechanism for raising a blister, and a cutter integrated in the body for cutting the blister produced on the skin.

Figure 4A:
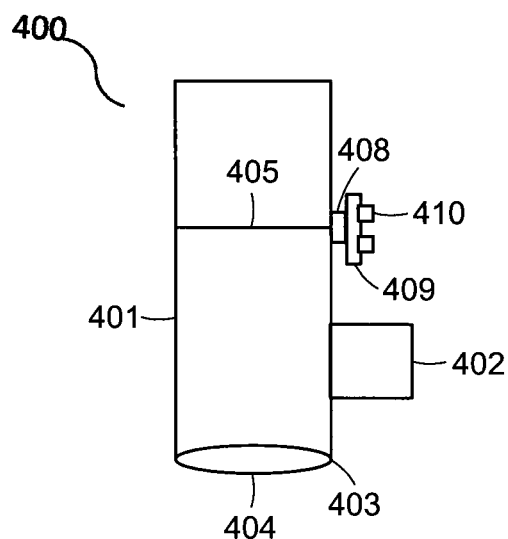
FIG. 4 panels A-B are drawings showing a device of the invention for raising a suction blister.
Figure 4B:
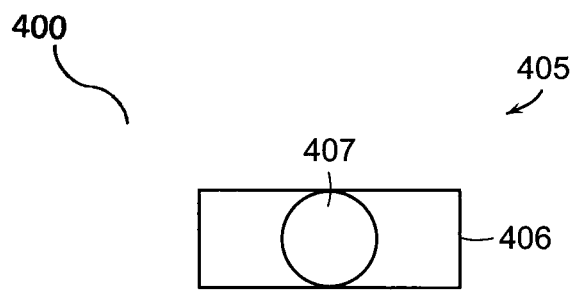
Figure 5A:
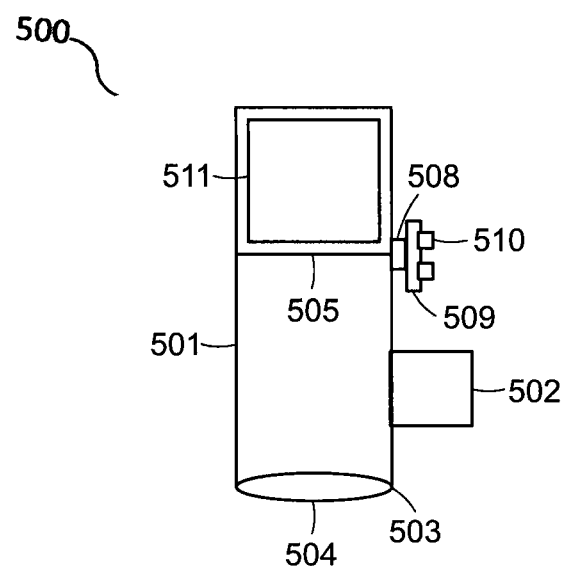
FIG. 5 panels A-D show different devices of the invention for raising a suction blister.
Figure 5B:
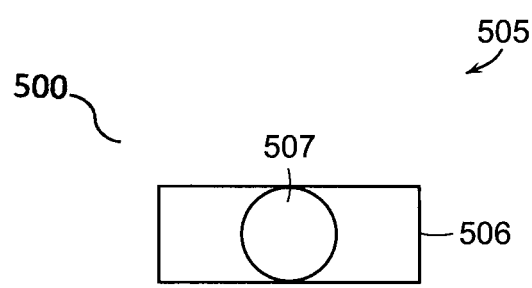
Figure 5C:
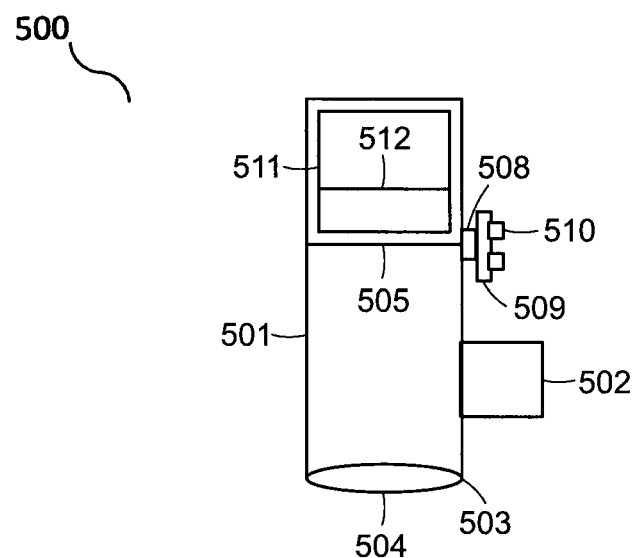
Figure 5D:
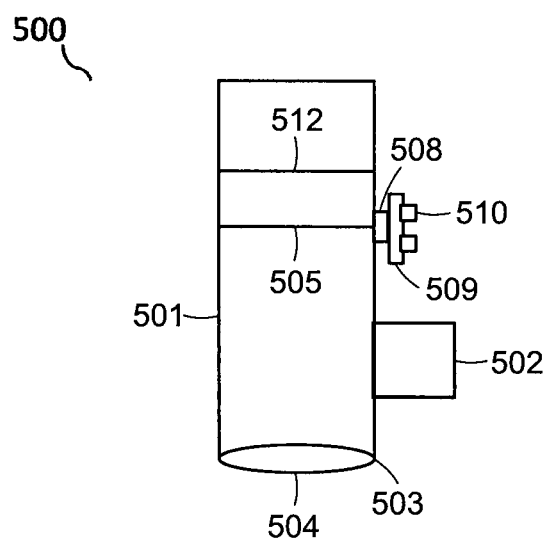

In certain embodiments, a device as shown in FIG. 4 panel A is used to obtain a skin graft. Device 400 includes a hollow body 401 and a mechanism for raising a blister 402. Hollow body 401 includes a distal end 403 that is configured for placement on the skin. Such a distal end may include an orifice plate 404. Orifice plate 404 determines the size and the shape of the blister or blisters that will be raised. Orifice plate 404 may be any shape or size and will depend on the blister or blisters to be raised. Generally, the diameter or lateral dimension of the blister may be from about 6 mm to about 12 mm, although larger or smaller blister sizes may be used.

The mechanism for raising a blister may be a vacuum component, a heating component, or a combination thereof. An exemplary heating component is a light source. In a particular embodiment, mechanism 402 is a combination of a vacuum component and a heating component.

The hollow body 401 further includes a cutter 405, which includes cutter plate 406 and a hole 407 (FIG. 4 panel B). Device 400 further includes an actuation block 408, actuation bar 409, and actuation block guides 410. Actuation components 408, 409, and 410 control movement of the cutter 405.

Blister formation is accomplished by attaching the distal end 403 of hollow body 401 to donor site of a patient, such as an inner thigh of a patient. Hook and loop fastener straps may be used to keep the device in place. The heating component of blister raising mechanism 402 provides a slight warming of orifice plate 404, which is in direct contact with the patient's skin surface. The application of a moderate negative pressure to the chamber interior from the vacuum component of blister raising mechanism 402, results in the patient's skin being gently drawn through the opening in orifice plate 404. The result is a blister or blisters, approximately the size of the opening in orifice plate 404. The produced blister may be fluid-filled or may not contain any fluid, i.e., a blister having air within. The skin and blister area is generally not damaged and patient discomfort is minimal.

The cutter 405 is positioned in hollow body 401 such that upon raising the blister, at least a portion of the blister protrudes through hole 407 in cutter plate 406. The actuation components 408, 409, and 410 are engaged to move cutter plate 406. The movement of cutter plate 406 disrupts the alignment of hole 407 with the other components of device 400, and results in cutting of the raised blister.

FIG. 5 panel A shows a device 500 that further includes a chamber 511 for capturing the cut blister. Chamber 511 is positioned in hollow body 501 and above cutter 505. Hollow body 501 includes a distal end 503 that is configured for placement on the skin. Such a distal end may include an orifice plate 504. The device 500 also includes a mechanism for raising a blister 502. The hollow body 501 further includes a cutter 505, which includes cutter plate 506 and a hole 507 (FIG. 5 panel B). Device 500 further includes an actuation block 508, actuation bar 509, and actuation block guides 510. Actuation components 508, 509, and 510 control movement of the cutter 505. Chamber 511 may be removable from device 500. Chamber 511 may include multiple configurations. For example, chamber 511 may include a retractable bottom. The bottom is in an open position when chamber 511 is inserted into hollow body 501. In the open position, chamber 511 is able to receive the cut blister. Once the cut blister is in chamber 511, the bottom of the chamber is closed, capturing the blister in chamber 511. Chamber 511 may then be removed from device 500.

In another embodiment, chamber 511 includes a substrate 512 (FIG. 5 panel C). In this embodiment, device 500 is configured such that substrate 512 is positioned in chamber 511 so that upon raising the blister, a portion of the blister contacts the substrate and becomes attached to the substrate. Cutter 505 then cuts the blister, and the cut blister becomes attached to the substrate 512 in chamber 511. Chamber 511 is then removed from device 500, and substrate 512 may be removed from chamber 511. In other devices, a vacuum, instead of a substrate, is used to hold the cut blister within the chamber.

In certain embodiments, device 500 does not use a chamber, rather a substrate 512 is directly integrated with device 500 in order to capture the cut blister (FIG. 5, panel D). Once captured, substrate 512 having an attached cut blister may be removed from device 500.

Methods of the invention may be used to prepare a skin graft to repair numerous different types of skin damage. For example, methods of the invention may be used to prepare grafts to treat burns (e.g., both thermal and chemical burns), blistering, dermatological conditions (e.g., epidermolysis bullosa or pyoderma gangrenosum), radiation therapy ulcers, diabetic ulcers, ischemic ulcers, trophic ulcers, trauma, or depigmentation (e.g., vitiligo).

In particular embodiments, methods of the invention are used to prepare a skin graft(s) to treat vitiligo. Vitiligo is a chronic disorder that causes depigmentation of patches of skin. It occurs when melanocytes, the cells responsible for skin pigmentation, die or are unable to function. Although patches are initially small, they often enlarge and change shape. When skin lesions occur, they are most prominent on the face, hands and wrists. Some lesions have hyper-pigmentation around the edges. Depigmentation is particularly noticeable around body orifices, such as the mouth, eyes, nostrils, genitalia and umbilicus.

Vitiligo is generally classified into two categories, non-segmental vitiligo and Segmental vitiligo. In non-segmental vitiligo (NSV), there is usually some form of symmetry in the location of the patches of depigmentation. New patches also appear over time and can be generalized over large portions of the body or localized to a particular area. Vitiligo where little pigmented skin remains is referred to as vitiligo universalis. Non-segmental vitiligo can come about at any age, unlike segmental vitiligo which is far more prevalent in teenage years.

Segmental vitiligo (SV) differs in appearance, aetiology and prevalence from associated illnesses. Its treatment is different from that of non-segmental vitiligo. It tends to affect areas of skin that are associated with dorsal roots from the spine. It spreads much more rapidly than non-segmental vitiligo and, without treatment, it is much more stable/static in course and not associated with auto-immune diseases.

FIG. 6 is a process chart showing steps for treating vitiligo using methods of the invention. To treat vitiligo, an autograft is provided to the site of depigmented skin. The graft includes melanocytes, and thus upon the recipient site accepting the graft, the graft will produce pigmented skin at the recipient site. As shown in FIG. 6, a donor site of pigmented skin is aseptically cleaned prior to harvesting of a skin graft. Standard methods are used to clean the donor site. A typical donor site is an inner thigh, but any area of pigmented skin may be used.

After cleaning, a skin grafted is harvested by raising a blister, such as a suction blister, and cutting the blister. Devices described herein may be used to raise and cut the blister. Alternatively, commercially available blister devices may be used. Once cut, the epidermal blister is placed onto a sterile cutting apparatus and divided into an array of micrografts. The micrografts are transferred to a first substrate for expansion. Transfer may occur as described above. In certain embodiments, the cut blister is placed directly onto the first substrate and the array of micrografts are generated directly on the first substrate. The micrografts are expanded as the surface area of the first substrate is expanded. The expanded micrografts are transferred to a second substrate. FIG. 6 shows an exemplary substrate, TEGADERM (medical dressing, commercially available from 3M, St. Paul, Minn.). However, any biocompatible substrate may be used.

The area of depigmented skin (i.e., the recipient site), is prepared through aseptic cleaning and dermabrasion. The second substrate including the expanded micrografts is applied to the dermabraded recipient site. The donor site and the recipient site are dressed and wound care is provided.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for applying a skin graft, the method comprising the steps of:
    providing a device comprising a negative pressure chamber with a removable cap, an orifice plate removably fitted to a lower end of the chamber and having a plurality of openings through which skin blisters can be raised, a cutter comprising a cutter plate having at least one hole, the cutter integrated and fitted within the chamber above the orifice plate such that at least a portion of the blisters protrudes through the at least one hole in the cutter and being movable within the chamber, and at least one light source coupled to the chamber and configured to deliver radiative energy into the chamber for heating an interior of the chamber and the orifice plate;
    contacting the orifice plate to skin at a donor site;
    utilizing said at least one light source to heat the interior of the chamber and the orifice plate with radiative energy, thereby warming the skin at the donor site so as to facilitate formation of skin blisters through said openings;
    raising a plurality of suction blisters through the openings in the orifice plate; and
    actuating the cutter to harvest said plurality of suction blisters.

2. The method according to claim 1, wherein the method further comprises: maintaining temperature of the orifice plate at a preset value.

3. The method according to claim 2, wherein said preset value is 40° Celsius.

4. The method according to claim 3, further comprising applying the harvested blisters to a recipient site.

5. The method according to claim 4, wherein the recipient site is an area of depigmented skin that has been prepared to receive the harvested blisters.

6. The method according to claim 1, further comprising harvesting the plurality of suction blisters onto a substrate.

7. The method according to claim 6, further comprising stretching the substrate.

8. The method according to claim 6, further comprising transferring the harvested blisters from said substrate to a second substrate.

9. The method according to claim 1, wherein the harvested blisters are utilized as an autograft.

10. A method of skin grafting, the method comprising the steps of:
    providing a device comprising a negative pressure chamber with a removable cap, an orifice plate removably fitted to a lower end of the chamber and having a plurality of openings through which skin blisters can be raised into an interior of the chamber, and a cutter comprising a cutter plate having at least one hole, the cutter integrated and fitted within the chamber above the orifice plate such that at least a portion of the blisters protrudes through the at least one hole in the cutter and being movable within the chamber, and at least one light source coupled to the chamber and configured to deliver radiative energy into the chamber for heating an interior of the chamber and the orifice plate;

contacting the orifice plate to skin at a donor site;

utilizing said at least one light source to heat the interior of the chamber and the orifice plate with radiative energy, thereby warming the skin at the donor site so as to facilitate formation of skin blisters through said openings;

utilizing a temperature controller to maintain temperature of said heated orifice plate at a preset value;

raising a plurality of suction blisters through the openings in the orifice plate; and actuating the cutter to harvest said plurality of suction blisters.

11. The method according to claim 10, further comprising applying said harvested blisters to a recipient site.

12. The method according to claim 11, wherein the recipient site is an area of depigmented skin that has been prepared to receive the harvested blisters.

13. The method according to claim 10, wherein said temperature controller maintains the temperature of the orifice plate at 40° Celsius.

14. The method according to claim 10, wherein the method further comprises:

harvesting the plurality of suction blisters onto a substrate; and stretching the substrate.

15. The method according to claim 14, wherein the method further comprises:

transferring the harvested blisters from said substrate to a second substrate.

16. The method according to claim 15, wherein the substrates are medical dressings.

17. The method according to claim 15, wherein the substrates are the same material.

18. The method according to claim 15, wherein the substrates are different materials.

19. The method according to claim 10, wherein the harvested blisters are utilized as an autograft.

\* \* \* \* \*